United States Patent [19]

Shimizu et al.

[11] 4,287,376
[45] Sep. 1, 1981

[54] METHOD FOR ARALKYLATION

[75] Inventors: Isoo Shimizu; Okitsugu Tsuji, both of Yokohama; Eiichi Matsuzaka; Atsushi Sato, both of Tokyo, all of Japan

[73] Assignee: Nippon Petrochemicals Co., Ltd., Tokyo, Japan

[21] Appl. No.: 60,662

[22] Filed: Jul. 25, 1979

[30] Foreign Application Priority Data

Aug. 10, 1978 [JP] Japan ................................. 53-97537

[51] Int. Cl.$^3$ .............................................. C07C 2/66
[52] U.S. Cl. .................................................. 585/458
[58] Field of Search .......................................... 585/458

[56] References Cited

U.S. PATENT DOCUMENTS 2,564,077  8/1951  Proell ................................. 585/458

FOREIGN PATENT DOCUMENTS

48/44240  6/1973  Japan .
52/14805  3/1977  Japan .
585073    1/1947  United Kingdom .
896864    5/1962  United Kingdom .
959355    6/1964  United Kingdom .
977322    12/1964 United Kingdom .

Primary Examiner—Curtis R. Davis
Attorney, Agent, or Firm—Fisher, Christen and Sabol

[57] ABSTRACT

A method for aralkylation of benzene or alkylbenzenes which is characterized in that an aromatic olefin having a double bond or double bonds which are conjugated with the benzene ring is added to the benzene or alkylbenzenes in the presence of at least one member of catalyst selected from the group consisting of the compounds represented by the general formula:

$$C_nF_{2n+1-m}Cl_mSO_3H$$

in which the symbol n is an integer from 1 to 5 and m is 0 or 1. Since the selectivity to the aromatic olefin in the reaction is excellent, the mixture of aromatic olefins and aliphatic olefins can be employed as one of the starting material.

10 Claims, No Drawings

1

METHOD FOR ARALKYLATION

BACKGROUND OF THE INVENTION

1. Field of the Invention

This invention relates to a method for aralkylation of benzene and alkylbenzenes (hereinafter totally referred to as "alkylbenzenes"). More particularly, the invention relates to a method for aralkylation in which, when an olefin or a mixture of olefins and alkylbenzenes are subjected to addition reaction, only the aromatic olefins having double bonds that are conjugated with benzene rings (hereinafter referred to as "styrenes") are selectively aralkylated.

2. Description of the Prior Art

The addition of several olefins to alkylbenzenes is well known as one of Friedel-Crafts reactions since it is very important in view of chemical industry. The addition reactions are defined such that the reaction between alkylbenzenes and aliphatic double bond compounds (hereinafter referred to as "aliphatic olefins") is alkylation and the reaction between styrenes and alkylbenzenes is aralkylation. By the way, the term "olefins" includes both aliphatic olefins (including diolefins) and armomatic olefins (including styrenes). These definitions shall apply hereinafter.

The alkylated compounds are used as starting materials in chemical industry and the compound themselves are used as insulating oils, lubricating oils and so forth. Meanwhile, the aralkylated compounds are excellent in thermal stability, compatibility and electrical characteristics, so that they are industrially suitable as desirable aromatic synthetic oils for heat transfer medium, plasticizer, solvent, reaction medium and insulating oil. There are, however, few instances of chemical works to produce solely the aralkylated compounds because of the difficulty in preparation thereof.

The basic chemical structure of the aralkylated compound that is aimed to prepare in accordance with the present invention has a skeletal structure of diphenylmethane in which a pair of benzene rings are joined to one carbon atom. Accordingly, the products prepared through the method of the present invention are characterized in that they are noncondensed polycyclic aromatic synthetic oils which are different from the well known high boiling aromatic synthetic oils such as alkyl naphthalene and alkyl biphenyl.

There are known some methods to prepare the aralkylated products. In one method, alkylbenzenes are aralkylated with using α-halogenated alkylbenzenes in the presence of metal halide catalysts such as aluminum chloride. In another method, alkylbenzenes are aralkylated with styrenes in the presence of acid catalysts. In the former method, it is necessary to recover and treat the by-product of hydrogen halide and the economical acquisition of aralkylating agents is difficult. However, the latter method for aralkylation with the use of styrenes in the presence of acid catalyst is desirable because it is free from such the disadvantages.

As the methods for aralkylation with styrenes that have already been disclosed, are the method to use sulfuric acid catalyst described in British Pat. No. 977,322 and the method to use solid acid catalyst described in British Pat. No. 896,864. However, the present inventors have confirmed the fact that, in both the above methods, the addition reaction of not only styrenes but also aliphatic olefins are caused to proceed. Therefore, when the prior art method is employed for the raw material containing both styrenes and aliphatic olefins, a mixture of aralkylation product and alkylation product is obtained because of the lack of selectivity to styrenes or aliphatic olefins. In order to prepare the aralkylation product solely, it is necessary to use previously isolated styrenes as raw materials and the use of such the expensive materials is disadvantageous in view of the industrial production.

BRIEF SUMMARY OF THE INVENTION

It is, therefore, the primary object of the present invention to provide a novel method for aralkylation which has selectivity to the aralkylation by styrenes.

Another object of the present invention is to provide a method for aralkylation in which the mixture of styrenes and aliphatic olefins can be employed as the starting materials without causing any disadvantage.

A further object of the present invention is to provide a method for aralkylation which can be put into practice in industrial scale economically without difficult in operation.

The present inventors have carried out wide and extensive investigation with regard to the aralkylation reaction, and as the result, a catalyst for selective aralkylation has newly been found, thereby accomplishing the present invention. The catalyst has activity only to the aralkylation with styrenes and no activity to the alkylation with aliphatic olefins, so that the non-condensed polycylic aromatic compounds having diphenyl methane structure can be prepared by using the starting material of the mixture containing various kinds of unsaturated hydrocarbons.

In accordance with the method of the present invention, the aralkylation products which is suitable for heat transfer media, plasticizers, several solvents and insulating oils having excellent practical characteristics can be produced selectively by using the starting material of crude fraction of petroleum distillation which contains both aliphatic olefins and styrenes.

When olefins are added to benzene or at least one of alkylbenzenes having an alkyl group or groups of 1 to 18 in total carbon atom number in accordance with the method of the present invention, the aralkylation of benzene or alkylbenzene is carried out at 5°–150° C. in the presence of catalyst which contains at least one of the compounds represented by the general formula:

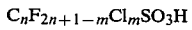

$C_nF_{2n+1-m}Cl_mSO_3H$ wherein the symbol n is an integer from 1 to 5, inclusive, and m is 0 (zero) or 1, thereby causing the addition of aromatic olefins which have double bonds that are conjugated to benzene rings.

DETAILED DESCRIPTION OF THE INVENTION

The aralkylation catalyst that is used in the method of the present invention is perhalogenoalkyl sulfonic acid represented by the general formula:

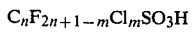

$C_nF_{2n+1-m}Cl_mSO_3H$ in which the symbol n is an integer from 1 to 5, inclusive, and m is 0 or 1. Exemplified as such catalysts are $CF_3SO_3H$, $CF_2ClSO_3H$, $C_2F_5SO_3H$, $C_3F_7SO_3H$, $C_4F_9SO_3H$ and $C_5F_{11}SO_3H$. In this sulfonic acid, chlorine atoms or flourine atoms are substituted for all the hydrogen atoms of its alkyl group and the dissociation of hydrogen ions is easily caused to occur by the electron donative property of the chlorine or fluorine. Therefore, it is very strong as an acid to exert an acidity that is stronger than that of 100% sulfuric acid and it is one of what is called "super acids", which are discussed in the reference of G. A. Olah, "Friedel-Crafts Chemistry", page 367, John Wiley & Sons, Inc. (1973).

The alkylbenzenes which are used in the method of the present invention include benzene and alkylbenzenes having an alkyl group or groups of 1 to 18 in total carbon atom number. When the total carbon atom number of the alkyl groups of the alkylbenzene is 19 or more, the dealkylation or isomerization of alkyl groups is caused to occur so that the aimed aralkylated alkylbenzene can not be obtained in good yield. The alkyl groups include straight chain alkyl groups, branched chain alkyl groups and cycloalkyl groups such as those of indane and tetralin. Exemplary of the alkylbenzenes are benzene, lower alkylbenzenes such as toluene, o-xylene, m-xylene, p-xylene, ethylbenzene, 1,2,3-trimethylbenzene, 1,2,4-trimethylbenzene, 1,3,5-trimethylbenzene, o-ethyltoluene, m-ethyltoluene, p-ethyltoluene, n-propylbenzene and cumene, higher alkylbenzenes having alkyl groups of 4 to 18 in carbon atom numbers, and the compounds having cycloalkyl groups such as the structures of indane and tetralin. These examples by no means restrict the present invention. These alkylbenzenes can be used in the method of the present invention either solely or in combination of two or more kinds. Further, even when the fraction of the above alkylbenzene contains aliphatic hydrocarbons, the method of the present invention can be performed without any trouble.

The other starting materials of olefins which are used for the aralkylation of the present invention are the compounds which have a double band or double bonds at the position at which the double bonds conjugate with benzene rings (hereinafter referred to as "styrenes"). Exemplified as such the styrenes are styrene, alkyl derivatives of styrene such as α-methyl-styrene, β-methylstyrene and vinyltoluene, the compounds having two double bonds at the positions at which the double bonds conjugate with benzene rings such as divinylbenzene and its alkyl derivatives, and the compounds having the cyclic side chains with double bonds which conjugate with benzene ring such as indene and alkylindene. In the method of the present invention, these styrenes can be used either solely or in combination of two or more kinds.

Further, included in the raw materials which can be advantageously used in the method of the present invention are aromatic by-product oils having boiling points in the range of 65° to 198° C. (hereinafter referred to as "aromatic by-product oil") which are obtained in the thermal cracking of petroleum hydrocarbons at a temperature of 700° C. or higher for the purpose of producing ethylene. The compositions of the by-product oils vary according to the kinds of raw material oils that are fed into cracking devices and the conditions of cracking. However, they are mixtures of the compounds having 5–10 carbon atoms varying in the ranges of 1–15 wt % of saturated aliphatic hydrocarbons, 35–85 wt % of aromatics of alkylbenzenes, 2–10 wt % of aliphatic olefins and 2–15 wt % of styrenes. The fraction of by-product oil having a boiling point above 198° C. obtained from the thermal cracking is not desirable because it contains naphthalene and other condensed-type polycyclic aromatic components. In the following Table 1, exemplary analytical data of aromatic by-product oils are shown.

TABLE 1

| | Composition of Aromatic By-Product Oil (% by weight) | | | | |
|---|---|---|---|---|---|
| Hydrocarbon | Saturated aliphatic hydrocarbons | Alkyl benzenes | Aliphatic olefins | Styrenes | Total |
| $C_5$ | 4.2 | — | 3.9 | — | 8.1 |
| $C_6$ | 7.3 | 33.4 | 4.7 | — | 45.4 |
| $C_7$ | 1.1 | 19.9 | 0.9 | — | 21.9 |
| $C_8$ | 0.7 | 10.5 | 0.6 | 4.9 | 16.7 |
| $C_9$ | 0.3 | 4.4 | 0.2 | 2.3 | 7.2 |
| $C_{10}$ | 0.1 | 0.3 | 0.1 | 0.2 | 0.7 |
| Total | 13.7 | 68.5 | 10.4 | 7.4 | 100.0 |

Apart from the above brief explanation, it should be noted that the use of isolated styrenes such as styrene and/or α-methylstyrene which do not contain aliphatic olefins for the method of the present invention, constitutes also the working of the present invention.

The quantity of the catalyst to be used in the method of the present invention is 0.01 mol % or more to alkylbenzenes, one of reaction materials. Within the above range, the quantity of the catalyst can be optionally selected and the increase in the concentration of catalyst does not affect the selectivity in the aralkylation. However, in order to reduce the reaction time and enhance the reaction efficiency, the quantity of catalyst may preferably be 0.1 mol % or more.

The desirable temperature of reaction is in the range of 5° C. to 150° C., inclusive. The temperature below 5° C. is not desirable because styrenes polymerize and the yield of aimed aralkylated product is lowered. On the other hand, when the reaction temperature exceeds 150° C., the yield of the aimed product is also reduced by the increase of the loss of styrenes with their thermal polymerization and the dealkylation and isomerization of alkylbenzenes. In the method of the present invention, the reaction temperature can be freely selected within the range of the above-mentioned 5° C. to 150° C., however, it is necessary that the alkylbenzenes and styrenes must be maintained in liquid state. When pressure is applied, the level of pressure is natually changed according to the kinds of alkylbenzenes and styrenes used for the reaction. As far as the raw materials are maintained in liquid state, the level of pressure may be selected optionally. This pressure is generally not higher than 50 kg/cm$^2$G. The reaction time can also be selected, for example, it may be in the range of 0.1 to 100 hours.

The reaction products that are prepared through the method of the present invention are 1:1 adduct in which one molecule of styrene is added to one molecule of alkylbenzene and 1:2 adduct in which two molecules of styrene are added to one molecule of alkylbenzene. The 1:1 adduct and 1:2 adduct will be described by taking xylene and styrene as the examples of starting materials. The 1:1 adduct is monostyrenated xylene (1-xylyl-1-phenylethane). In the case that mixed xylene is used, the mixture of four kinds of isomers are produced according to the four kinds of xylene isomers (o-, m- and p-xylenes and ethylbenzene). The 1:1 adduct gives a single peak of 210 in the molecular weight measurement (hereinafter referred to as "m/e value") in mass spectrometry, and the adduct is a liquid having a boiling point of 292°–305° C. at atmospheric pressure. The 1:2 adduct is made by adding two moles of styrene to one mole of xylene and it gives a single peak of 314 in m/e value. When mixed xylene is used, a mixture of several kinds of isomeric products are obtained according to the kinds of four isomers and the positions of the addition of styrene. The boiling point of this 1:2 adduct is 180°–240° C. at a reduced pressure of 3 mmHg. Further the heavier reaction product is the polymer of styrene which is not desirable, so that the formation of such the polymer must be avoided.

The molar ratio of alkylbenzenes and styrenes that are fed into the reaction system until the end of reaction according to the present invention, can be optionally selected with the maximum of 1:2. Therefore, the ratio of reaction product may be varied within the range of:

(1:1 adduct):(1:2 adduct)=1:0.91~1:0.01.

The use of excess styrene over this molar ratio, 1:2, is not desirable since the ratio of conversion into the aimed product is reduced.

The above 1:1 adduct can be used, for example, as the solvent of dyes for pressure-sensitive recording paper, a capacitor oil, especially as the impregnating oil for capacitors in which plastic film such as polypropylene film is used partially or totally as the dielectrics, the oil for oil filled cables, electrically insulating oil such as transformer oil, heat transfer medium, diluent for epoxy resin, softening agent or plasticizer for synthetic resins and elastomers, softening agent or plasticizer for synthetic resin adhesives and elastomer adhesives, hydraulic oil, and so forth.

The 1:2 adduct is used, for example, as plasticizer for Thiokol (trademark of the product of Thiokol Chem. Corp.) and other sealant, electrically insulating oil, plasticizer for paints, plasticizer for synthetic resins and elastomers, and softening agent or plasticizer for synthetic resin adhesives and elastomer adhesives. Furthermore, the nucleus hydrogenation products of these 1:1 adduct and 1:2 adduct can be used for the above purposes and as traction drive oil and other lubricating oils. It should be noted, of course, that the product obtained by the method of the present invention is not restricted to the above uses.

In order that those skilled in the art may better understand the present invention and the manner in which it may be practised, the following specific examples and comparative examples are given.

EXAMPLE 1

A 50 ml test tube was fed with 10 g of o-xylene and 0.05 of a catalyst of trifluoromethane sulfonic acid and, with shaking the test tube in a water bath at 50° C., 3 g of 1:1 (by weight) mixture of styrene and octene-1 was fed dropwise into the test tube. After the dropping, the reaction mixture was neutralized and washed with water and the light fraction was removed by treating the mixture at a temperature of 95° C. and a pressure of 3 mmHg. The remained liquid reaction product gave a peak of 210 in m/e value, thus it was 1:1 adduct of o-xylene and styrene. Since the peak of 218 in m/e value which corresponds to the adduct of octene-1 and xylene was not observed, it was understood that the octene-1 did not participate in the reaction.

EXAMPLE 2

In order to confirm the selectivity to the alkylation and aralkylation in this example, the following alkylbenzenes and olefins are separately used and the reaction was carried out in like manner as the foregoing Example 1. The confirmation of reaction products after the reaction was done by measuring the m/e values.

The employed alkylbenzenes were eight kinds, i.e., benzene, toluene, o-xylene, pseudocumene, t-butylbenzene, t-amylbenzene, n-octylbenzene and n-dodecylbenzene.

Used aliphatic olefins were twelve kinds, i.e., octene-1, octene-2, 2-ethylhexene-1, 2,4,4-trimethylpentene-1, 2,4,4-trimethylpentene-2, 1,3-cyclooctadiene, 1,5-cyclooctadiene, 1,7-octadiene, cyclooctene, 2,5-dimethyl-2,4-hexadinee, 2,4-dimethylcyclohexene and ethylidenecyclohexane.

Further, used styrenes were five kinds of styrene, α-methylstyrene, β-methylstyrene, vinyltoluene and indene, and allylbenzene as the aromatic olefin in which the double bond is not conjugated with benzene ring.

The results of the tests are shown in the following Table 2. By measuring m/e values of reaction products, the formation of theoretically led aralkylated compounds and alkylated compounds was confirmed. In the Table 2, the symbols "o" represent that the formation of the addition products between the unsaturated compounds and the alkylbenzenes was confirmed and the symbols "x" represent that the formation of such the products was not confirmed.

TABLE 2

| Unsatd. Comp. | Alkylbenzene | | | | | | | |
|---|---|---|---|---|---|---|---|---|
| | Benzene | Toluene | o-Xylene | Pseudo-cumene | t-Butyl benzene | t-Amyl benzene | n-Octyl benzene | n-Dodecyl benzene |
| Octene-1 | x | x | x | x | x | x | x | x |
| Octene-2 | x | x | x | x | x | x | x | x |
| 2-Ethylhexene-1 | x | x | x | x | x | x | x | x |
| 2,4,4-Trimethyl pentene-1 | x | x | x | x | x | x | x | x |
| 2,4,4-Trimethyl-pentene-2 | x | x | x | x | x | x | x | x |
| 1,3-Cyclooctadiene | x | x | x | x | x | x | x | x |
| 1,5-Cyclooctadiene | x | x | x | x | x | x | x | x |
| 1,7-Octadiene | x | x | x | x | x | x | x | x |
| Cyclooctene | x | x | x | x | x | x | x | x |
| 2,5-Dimethyl-2,4-hexadiene | x | x | x | x | x | x | x | x |
| 2,4-Dimethyl-cyclohexene | x | x | x | x | x | x | x | x |
| Ethylidenecyclo-hexane | x | x | x | x | x | x | x | x |
| Styrene | o | o | o | o | o | o | o | o |
| α-Methylstyrene | o | o | o | o | o | o | o | o |
| β-Methylstyrene | o | o | o | o | o | o | o | o |

TABLE 2-continued

| | Alkylbenzene | | | | | | | |
|---|---|---|---|---|---|---|---|---|
| Unsatd. Comp. | Benzene | Toluene | o-Xylene | Pseudo-cumene | t-Butyl benzene | t-Amyl benzene | n-Octyl benzene | n-Dodecyl benzene |
| Vinyltoluene | o | o | o | o | o | o | o | o |
| Allylbenzene | x | x | x | x | x | x | x | x |
| Indene | o | o | o | o | o | o | o | o |

As will be understood from the results of Table 2, the selectivity to styrene among the aliphatic olefins of styrenes is quite good irrespective of the kinds of alkylbenzenes. Further, the allylbenzene, one of aromatic olefins, has no double bond which is conjugated with the benzene ring so that it is inactive in the reaction.

EXAMPLE 3 reaction vessel was fed with 780 g of benzene and 10 g of the catalyst of trifluoromethane sulfonic acid and the contents in the reaction vessel were maintained at 60° C. by heating with stirring. While, 170 g of an aliphatic olefin mixture mainly containing propylene tetramer (boiling range: 185°–210° C., average molecular weight: 170) and 118 g of a vinyltoluene mixture (weight ratio of meta:para isomers—65:35) were mixed together. This mixture was added dropwise into the reaction vessel where the reaction temperature was kept at 60°±2° C. After the addition, the catalyst was removed and the reaction product was neutralized and washed with water. It was then subjected to distillation at atmospheric pressure to remove 860 g of the light fraction up to the distilling temperature of 220° C. and the remainder was further subjected to distillation under reduced pressure of 3 mmHg to obtain 170 g of first fraction of 130°–155° C. in distilling temperature, 22 g of second fraction 190°–220° C., and 9 g of distillation residue. The first fraction gave a single peak of 196 in m/e value which corresponds to the 1:1 adduct of benzene and vinyltoluene and the second fraction gave a single peak of 314 in m/e value which corresponds to the 1:2 adduct of benzene and vinyltoluene. The peaks of the adducts of propylene tetramer of 246 (dodecylbenzene) and 414 (didodecylbenzene) in m/e values were not observed in both the first and second fractions. Therefore, it has been understood that the selectivity to the aromatic olefins among the aliphatic olefins and aromatic olefins is quite good.

EXAMPLE 4

The aromatic by-product oil as shown in the foregoing Table 1 as exemplary analytical data, was used in this example. A mixture of 100 g of toluene and 10 g of trifluoromethane sulfonic acid was heated with stirring and maintained at a temperature of 40°±5° C. Then, 100 g of the aromatic by-product oil was added dropwise to the above mixture in 3 hours. After the dropping, the reaction was further contained for 30 minutes at 40° C. with stirring, and after the reaction, the catalyst was removed from the reaction product, which was further neutralized and washed with water. Then, 960 g of a light fraction up to the distilling temperature of 225° C. was removed by atmospheric pressure distillation. Further, the remainder was subjected to reduced pressure distillation at 3 mmHg and 110 g of a first fraction of 135°–170° C. in distilling temperature, and 25 g of a second fraction of 190°–240° C. were obtained.

The first fraction was a mixture giving the m/e peak distribution of 182, 196, 210, 224, 238 and 242. All the components of this fraction were diphenylmethane type compounds ($C_nH_{2n-14}$). The second fraction was a mixture giving the m/e peak distribution of 286, 300, 314 and 328 and was composed of triphenylmethane type compounds ($C_nH_{2n-22}$). In the above test results, the reaction products of $C_nH_{2n-6}$ as the adducts of aliphatic olefins were not observed.

EXAMPLE 5-7

In each example, 530 g of m-xylene and a prescribed quantity (see Table 3) of the catalyst of trifluoromethane sulfonic acid were fed into a reaction vessel and the contents were maintained at 130°±5° C. with stirring. Then, 104 g of styrene was added dropwise to the above mixture in 1 hour. After the dropping of the styrene, the reaction product was neutralized and washed with water. By reduced pressure distillation at 3 mmHg, a fraction in the range of 125°–140° C. was obtained. This fraction gave a single peak of 210 in m/e value which corresponds to 1:1 adduct of styrene and m-xylene. The results of the tests are shown in the following Table 3.

TABLE 3

| Example | Catalyst (g) | Yield of fraction (g) | Yield of styrene (%) |
|---|---|---|---|
| 5 | 0.8 | 150 | 71 |
| 6 | 4 | 190 | 90 |
| 7 | 7.5 | 195 | 93 |

In the above Table, the yield of styrene means the molar percent of styrene which was converted into the aimed 1:1 adduct relative to the total styrene that was used for the reaction.

EXAMPLES 8 AND 9

A reaction vessel was fed with 740 g of t-amylbenzene and 5 g of trifluoromethane sulfonic acid and 140 g of styrene was then added dropwise in 1 hour at a prescribed temperature. After the neutralization and water washing, the reaction mixture was subjected to reduced pressure distillation at 3 mmHg to obtain a fraction of 135°–165° C. in distilling temperature. This fraction gave a single peak of 252 in m/e value which corresponds to the 1:1 adduct of t-amylbenzene and styrene. The results of tests are shown in the following Table 4.

TABLE 4

| Example | Reaction temperature (° C.) | Yield of fraction (g) | Yield of styrene (%) |
|---|---|---|---|
| 8 | 135 ± 5 | 230 | 91 |
| 9 | 15 ± 5 | 220 | 87 |

EXAMPLES 10–14

In each example, a reaction vessel was fed with 1060 g of o-xylene and 15 g of the catalyst of trifluoromethane sulfonic acid and the prescribed quantity of styrene was further added to cause the reaction at a temperature of 60°±5° C. After the reaction, the reaction mixture was neutralized and washed with water, and then it was subjected to distillation under a reduced pressure of 3 mmHg. Through the distillation, a first fraction of the 1:1 adduct of 130°–155° C. in distilling temperature and a second fraction of the 1:2 adduct of 180°–230° C. were obtained. The results of the tests are shown in the following Table 5.

TABLE 5

| Example | Feed of styrene (g) | Molar ratio of styrene/xylene | First fraction (g) | Second fraction (g) | Yield of sytrene (g) |
|---|---|---|---|---|---|
| 10 | 624 | 0.6 | 1100 | 15 | 90 |
| 11 | 1040 | 1.0 | 1315 | 420 | 90 |
| 12 | 1456 | 1.4 | 1240 | 955 | 87 |
| 13 | 1878 | 1.8 | 1185 | 1080 | 72 |
| 14 | 2288 | 2.2 | 1050 | 1150 | 55 |

In the above Table, the yield of styrene represents the molar percent of styrene which was converted into the aimed first fraction and the second fraction relative to the styrene used for the reaction. In Example 14, the molar ratio of o-xylene to styrene was 1:2.2, from which it was understood that the yield of styrene became low with the increase of the molar ratio of styrene to xylene.

EXAMPLE 15

The reaction was carried out in like manner as Example 1 by using pseudocumene as the alkylbenzene, α-methylstyrene as the styrene and octene-1 as the aliphatic olefin. The concentration of the catalyst was regulated within the range of 0.1–0.05 mol % to the pseudocumene. Used catalysts were five kinds, i.e., $C_2F_5SO_3H$, $C_3F_7SO_3H$, $C_4F_9SO_3H$, $C_5F_{11}SO_3H$ and $CClF_2SO_3H$. From the results of these tests, it was understood that the adduct of the α-methyl styrene and the pseudocumene giving the m/e value of 238 was obtained but the adduct of the octene-1 and the pseudocumene was not formed.

EXAMPLE 16

The reaction was carried out in the same manner as Example 5 except that the quantity of catalyst was 0.07 g, in which the molar percent of the catalyst was 0.009 to the m-xylene. The yield of fraction was 115 g and the yield of styrene was 55%. This fraction contained the component of 208 in m/e value in addition to the component of 210 in m/e value. The component of m/e value 208 was the dimer which was formed by dimerization of the styrene without causing the aralkylation.

COMPARATIVE EXAMPLE 1

With using 97% sulfuric acid as a catalyst, the reaction was carried out in like manner as Example 3 and 315 g of fraction having the same distilling temperature as that of the first fraction of Example 3 was obtained. It was confirmed that this fraction contained $C_nH_{2n-6}$ type compounds of alkylated products of aliphatic olefins giving the m/e values of 204, 218, 232, 246, 260, 274 and 288 besides the vinyltoluene adduct of benzene of m/e 210.

COMPARATIVE EXAMPLES 2 AND 3

The reactions were carried out in the same manner as Example 8 except that the reaction temperatures were changed, the results of which are shown in the following Table 6.

TABLE 6

| Comparative Example | Reaction temperature (° C.) | Yield of fraction (g) | Yield of styrene (%) |
|---|---|---|---|
| 2 | 4 | 175 | 70 |
| 3 | 160 | 215 | 85 |

In the fraction of Comparative Example 2, the styrene dimer of m/e value 208 was contained in addition to the component of m/e value 252. Further, it was confirmed that the fraction of comparative Example 3 contained the components of m/e values 192 and 312 which were the products of elimination and disproportionation of the t-amyl groups, besides the aimed product of m/e value of 252.

COMPARATIVE EXAMPLE 4

A mixture of 34.5 g of nonadecylbenzene as the alkylbenzene and 0.1 g of the catalyst of trifluoromethane sulfonic acid was maintained at 130°±5° C. with stirring and 2.1 g of styrene was added dropwise thereto. After the dropping the reaction mixture was neutralized and washed with water and it was subjected to mass spectrometry. It was confirmed that the m/e value of nonadecylbenzene itself was not the single peak of 344 but the peaks of 344±14n (n is an integer) and the disproportionation, isomerization and elimination of alkyl groups were caused to occur.

Although the present invention has been described in connection with examples thereof, many variations and modifications will now become apparent to those skilled in the art. It is preferred, therefore, that the present invention be limited not by the specific disclosure herein but only by the appended claims.

What is claimed is:

1. In a method of aralkylation of at least one member selected from the group consisting of benzene and alkylbenzenes each having an alkyl group or groups of 1 to 18 in total carbon atom number by reacting at least one aromatic olefin each having a double bond or double bonds which are conjugated with the benzene ring thereof with said at least one member, the improvement in said method comprising carrying out said aralkylation in the presence of at least one catalyst selected from the group of compounds represented by the general formula:

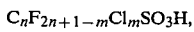

$$C_nF_{2n+1-m}Cl_mSO_3H,$$

in which the symbol n is an integer from 1 to 5, inclusive, and m is 0 (zero) or 1.

2. The improvement as claimed in claim 1, wherein said aralkylation is carried out at a temperature in the range of 5° to 150° C., inclusive.

3. The improvement as claimed in claim 1, wherein said at least one member and said at least one aromatic olefin are contained in a feed which is the fraction of thermal cracking by-product oil having a boiling range of 45° to 198° C. which is obtained when petroleum hydrocarbons are thermally cracked at a temperature of 700° C. or higher.

4. The improvement as claimed in claim 1, wherein a feed containing both aliphatic olefins and said aromatic olefins is used in said aralkylation.

5. The improvement as claimed in claim 1, wherein said catalyst is at least one member selected from the group consisting of $CF_3SO_3H$, $CF_2ClSO_3H$, $C_2F_5SO_3H$, $C_3F_7SO_3H$, $C_4F_9SO_3H$, and $C_5F_{11}SO_3H$.

6. The improvement as claimed in any one of claims 1, 2, 3, 4, or 5, wherein said allkylbenzenes are selected from the group consisting of toluene, o-xylene, m-xylene, p-xylene, ethylbenzene, 1,2,3-trimethylbenzene, 1,2,4-trimethylbenzene, 1,3,5-trimethylbenzene, o-ethyltoluene, m-ethyltoluene, p-ethyltoluene, n-propylbenzene, cumene, higher alkylbenzenes having alkyl groups of 4 to 18 carbon atoms, and cycloalkylbenzenes.

7. The improvement as claimed in any one of claims 1, 2, 3, 4, or 5, wherein said at least one aromatic olefin is selected from the group consisting of styrene, α-methylstyrene, β-methylstyrene and vinyltoluene, divinylbenzene and its alkyl derivatives, indene, and alkylindenes.

8. The improvement as claimed in any one of claims 1, 2, 3, 4, or 5 wherein said aralkylation is carried out at a temperature in the range of 5° C. to 150° C. and at a pressure sufficient to maintain said at least one member and said at least one aromatic olefin in the liquid state.

9. The improvement as claimed in any one of claims 1, 2, 3, or 4 wherein said catalyst is at least one member selected from the group consisting of $CF_3SO_3H$, $CF_2ClSO_3H$, $C_2F_5SO_3H$, $C_3F_7SO_3H$, $C_4F_9SO_3H$, and $C_5F_{11}SO_3H$.

10. The improvement as claimed in any one of claims 1, 2, 3, 4, or 5 wherein said alkylbenzenes are selected from the group consisting of toluene, o-xylene, m-xylene, p-xylene, ethylbenzene, 1,2,3-trimethylbenzene, 1,2,4-trimethylbenzene, 1,3,5-trimethylbenzene, o-ethyltoluene, m-ethyltoluene, p-ethyltoluene, n-propylbenzene, cumene, higher alkylbenzenes having alkyl groups of 4 to 18 carbon atoms, indane, and tetralin, and wherein said at least one aromatic olefin is selected from the group consisting of styrene, α-methylstyrene, β-methylstyrene, vinyltoluene, divinylbenzene and its alkyl derivatives, indenes and alkylindenes.

* * * * *